(12) United States Patent
Dimpfel et al.

(10) Patent No.: US 10,357,530 B2
(45) Date of Patent: Jul. 23, 2019

(54) COMBINATION OF VALERIAN ROOT EXTRACT AND LAVENDER OIL FOR USE IN THE TREATMENT OF SLEEP DISORDERS

(71) Applicant: Dr. Willmar Schwabe GmbH & Co. KG, Karlsruhe (DE)

(72) Inventors: Wilfried Dimpfel, Wetzlar (DE); Michael Nöldner, Karlsruhe (DE)

(73) Assignee: Dr. Willmar Schwabe GmbH & Co. KG, Karlsruhe (DE)

( * ) Notice: Subject to any disclaimer, the term of this patent is extended or adjusted under 35 U.S.C. 154(b) by 126 days.

(21) Appl. No.: 15/326,247

(22) PCT Filed: Jun. 10, 2015

(86) PCT No.: PCT/EP2015/062891
§ 371 (c)(1),
(2) Date: Jul. 10, 2017

(87) PCT Pub. No.: WO2016/008650
PCT Pub. Date: Jan. 21, 2016

(65) Prior Publication Data
US 2017/0296612 A1    Oct. 19, 2017

(30) Foreign Application Priority Data
Jul. 14, 2014    (EP) ..................... 14176927

(51) Int. Cl.
*A61K 36/84*    (2006.01)
*A61K 36/53*    (2006.01)

(52) U.S. Cl.
CPC .............. *A61K 36/84* (2013.01); *A61K 36/53* (2013.01); *A61K 2300/00* (2013.01)

(58) Field of Classification Search
None
See application file for complete search history.

(56) References Cited

U.S. PATENT DOCUMENTS

| 9,375,463 | B2 * | 6/2016 | Patel | .................... | A61K 36/185 |
| 2008/0124410 | A1 * | 5/2008 | Dienel | .................. | A61K 36/53 424/745 |
| 2009/0061029 | A1 * | 3/2009 | Rouda | .................... | A61K 36/28 424/746 |
| 2013/0004599 | A1 * | 1/2013 | Schwartz | .............. | A61K 36/84 424/733 |
| 2015/0283072 | A1 * | 10/2015 | Popitz | ................ | A61K 36/9068 424/736 |

FOREIGN PATENT DOCUMENTS

| CN | 103750535 A | * | 4/2014 |
| JP | 10025246 A | | 1/1998 |
| KR | 10-1296920 B1 | | 8/2013 |
| RU | 2 106 873 C1 | | 3/1998 |
| RU | 2215536 | * | 11/2003 |
| WO | WO 02/092113 A1 | | 11/2002 |
| WO | WO 2011 098394 | * | 8/2011 |
| WO | WO 2014 112676 | * | 7/2014 |

OTHER PUBLICATIONS

Basch E. et al. Lavender J of Herbal Pharmacotherapy 4(2)63-78, 2004 (Year: 2004).*
Dimpfel W. Early Effect of Neuropas Balance on Current Source Density of Human EEG. BMC Psychiatry 11:123 Aug. 2, 2011. (Year: 2011).*
Krylov et al., Manual on Phytotherapy. Peter, St. Petersburg. 2000; 317.
Maznev, Medicinal Plants. Moscow, Publishing House Lada. 2006; 256-260.
International Preliminary Report on Patentability dated Jun. 17, 2016 in connection with Application No. PCT/EP2015/062891.
International Search Report and Written Opinion dated Jul. 7, 2015 in connection with Application No. PCT/EP2015/062891.
Basch et al., Lavender (*Lavandula angustifolia* Miller). J Herb Pharmacother. 2004;4(2):63-78.
Braun, Herbs for Insomnia. Aust Fam Physician. Oct. 2008;89:70-1.
Dimpfel, Preclinical data base of pharmaco-specific rat EEG fingerprints (tele-stereo-EEG). Eur J Med Res. May 30, 2003;8(5):199-207.
Fibler et al., A case series on the use of lavendula oil capsules in patients suffering from major depressive disorder and symptoms of psychomotor agitation, insomnia and anxiety. Complement Ther Med. Feb. 2014;22(1):63-9. doi: 10.1016/j.ctim.2013.11.008.
Kim et al., Herbs for the Treatment of Insomnia. Biomol & Therap. Jul. 31, 2011;19(3):274-81.
Kraft, Schlaf-und psychische Störungen im Kindesalter / Sleep and psychiatric disorders in childhood. Zeitschrift für Phytotherapie. 2007;28:235-7.
Ramakrishnan et al., Treatment options for insomnia. Am Fam Physician. Aug. 15, 2007;76(4):517-26.
Koryo, Japan Perfumery & Flavoring Association. Dec. 20, 2011;(252):40-44.
Leathwood et al., Aqueous extract of valerian root (*Valeriana officinalis* L.) improves sleep quality in man. Pharmacol Biochem Behav. Jul. 1982;17(1):65-71.
Murphy et al., Valeriana officinalis root extracts have potent anxiolytic effects in laboratory rats. Phytomedicine. Jul. 2010;17(8-9):674-8. doi: 10.1016/j.phymed.2009.10.020. Epub Dec. 29, 2009.
Sivasubramanian, Effect of Valerian Root Extracts (*Valeriana officinalis*) on Acetaminophen Glucuronidation: in vitro and in vivo studies. University of Pittsburgh. 2005;166 pages.
PCT/EP2015/062891, dated Jul. 7, 2015, International Search Report and Written Opinion.
PCT/EP2015/062891, dated Jun. 17, 2016, International Preliminary Report on Patentability.

* cited by examiner

*Primary Examiner* — Ralph J Gitomer
(74) *Attorney, Agent, or Firm* — Wolf, Greenfield & Sacks, P.C.

(57) ABSTRACT

The present invention relates to a combination of valerian root extract and lavender oil treating of sleep disorders, as well as to a combination of preparation comprising valerian root extract and lavender oil.

8 Claims, 7 Drawing Sheets

COMBINATION OF VALERIAN ROOT EXTRACT AND LAVENDER OIL FOR USE IN THE TREATMENT OF SLEEP DISORDERS

CROSS-REFERENCE TO RELATED APPLICATION

This application is the National Phase under 35 U.S.C. § 371 of PCT International Application No. PCT/EP2015/062891, filed Jun. 10, 2015, which claims priority to European Patent Application No. 14176927.3, filed Jul. 14, 2014, the entire contents of the aforementioned applications are hereby incorporated herein by reference.

The present invention relates to a combination of valerian root extract (extract of dried roots of *Valeriana officinalis*) and lavender (oil of flowers of *Lavandula officinalis*) for oral treatment of sleep disorders.

The present invention relates to the use of a combination of lavender oil and valerian root extract as a highly potent sleep-inducing agent. The combination leads to a synergistic overadditive activity with respect to the induction and soundness of sleep.

Lavender oil is manufactured for different purposes and is used e.g. in aroma therapy. In particular, it is traditionally said to have a calmative effect. A special preparation for oral administration has been approved for several years as a medical agent in Germany for treating conditions of uneasiness and anxious depressive mood (Lasea® of Dr. Willmar Schwabe GmbH & Co. KG). Valerian root extract is traditionally used in case of nervous related sleep disorders and also exists as a medicament (e.g. "Baldiparan® Stark für die Nacht" of Pfizer Consumer Healthcare GmbH).

Although there are reports about possible biological or pharmacological effects of lavender oil for treating sleep disorders, no reliable clinical studies exist for this application. A combination with valerian root extract for improving sleep has not yet been described. Therefore, the finding that lavender oil is capable, despite the very weak effect on its own, to significantly enhance the effect of valerian root extract, or to multiply the same, respectively, is all the more surprising. Examinations in Tele-Stereo-EEG of rats within the frame of experiments of a different object revealed hints to the existence of such an overadditive, multiplying effect.

The presently common medical agents for treating sleep disorders show a broad spectrum of side effects (addiction and development of tolerance for benzodiazepines).

Thus, there is a considerable need for improved treatment possibilities for sleep disorders, either as medical agent or as food, with good efficiency at a low rate of side effects. This low rate of side effects is expected to be more likely in the administration of a natural compound or a combination of natural compounds.

This problem has surprisingly been solved by using lavender oil in combination with valerian root extract.

The invention relates to the combination comprising a content of valerian root extract (extract of dried roots of *Valeriana officinalis*) and lavender oil (oil of flowers of *Lavandula officinalis*) for use in the oral treatment or prophylaxis of sleep disorders, wherein the valerian root extract is prepared by extraction with aqueous ethanol or aqueous methanol, wherein ethanol and water are used in a volume ratio of 30/70 to 90/10 or methanol and water are used in a volume ratio of 40/60 to 55/45 in the extraction. The combination may optionally comprise further natural compounds from plants or extracts, however, it preferably does not comprise any further extracts from plants and/or oils from plants and/or other pharmaceutically active agents (drugs). The combination comprising valerian root extract and lavender oil for use in the treatment or prophylaxis of sleep disorders may be a dosage form, i.e. in the form of a medicament or food and may be present as two separate dosage forms, i.e. in the form of two separate medicaments or food, each of which contain the valerian root extract or the lavender oil, respectively. For the case that valerian root extract and lavender oil are present in separate dosage forms, e.g. in the form of a medicament or food, these can be administered simultaneously or subsequently in any order, i.e. valerian root extract first, followed by lavender oil, or lavender oil first and subsequently valerian root extract. The time sequence of administration should not be longer than an hour, preferably no longer than 30 minutes and particularly preferably no longer than 10 minutes. Preferably, also in case of separate administration, the valerian root extract and the lavender oil are administered simultaneously or almost simultaneously, i.e. within a few minutes (up to 10 minutes).

The following explanations refer to the oral use of the combination comprising valerian root extract and lavender oil according to the invention and optionally of pharmaceutically acceptable auxiliaries, or auxiliaries acceptable under food law in a medicament or food, respectively.

In vivo trials using rats show results confirming the superiority of the combination of lavender oil with an extract of valerian root. The overadditive and synergistic effect, which has been surprisingly found, has been document in vivo using rats, and was subsequently verified for the case of individual patients having sleep disorders.

Figure 4:
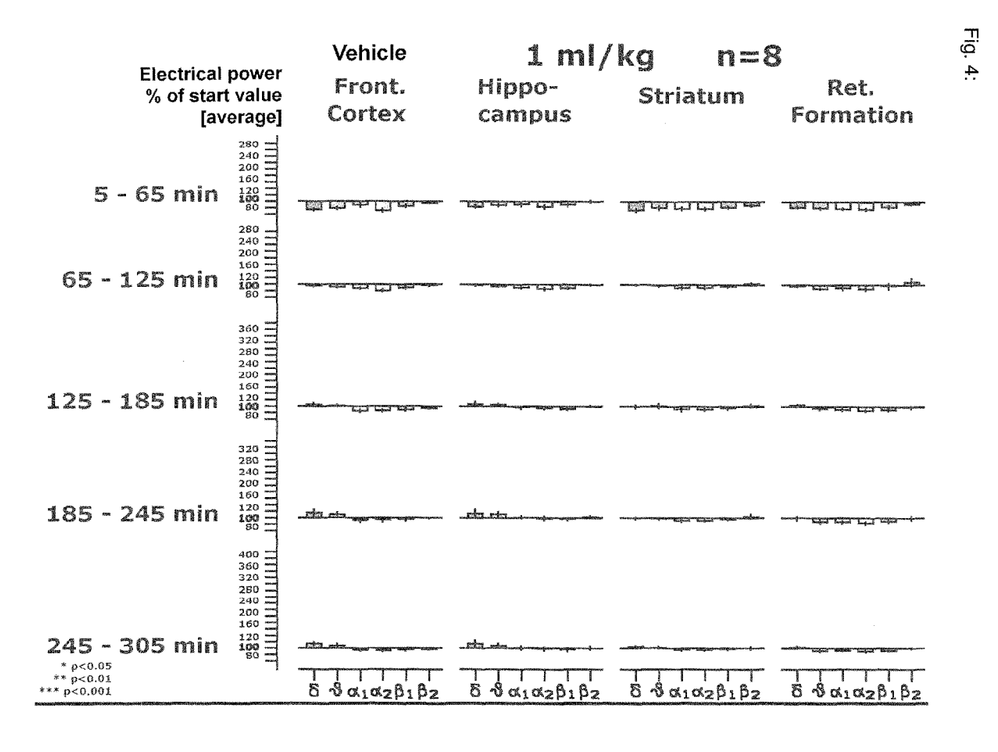
FIG. 4 Time course of electrical power of all frequency ranges during 5 hours after administration of vehicle (methyl cellulose) in four areas of the brain: frontal cortex, hippocampus, striatum and formatio reticularis. The six frequency ranges of delta (δ), theta (θ), alpha1 (α1), alpha2 (α2), beta1 (β1) and beta2 (β2) are documented on the x-axis.
Figure 5:
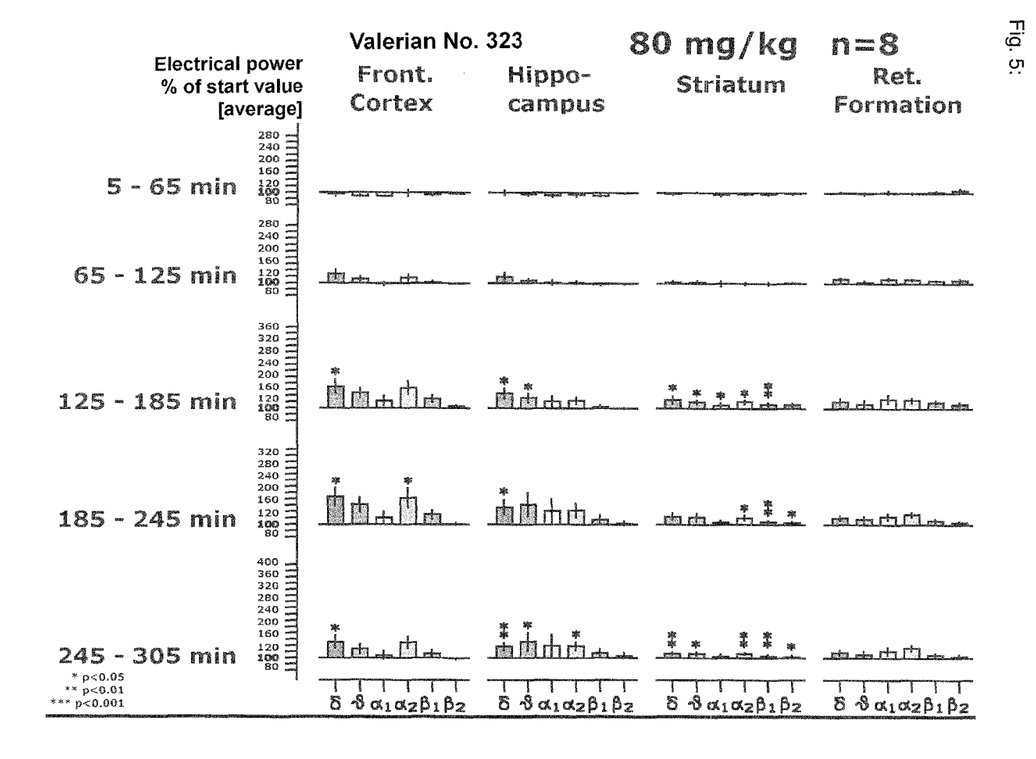
FIG. 5 Time course of electrical power of all frequency ranges during 5 hours after administration of 80 mg/kg of valerian root extract alone in four areas of the brain: frontal cortex, hippocampus, striatum and formation reticularis. The six frequency ranges of delta (δ), theta (θ), alpha1 (α1), alpha2 (α2), beta1 (β1) and beta2 (β2) are documented on the x-axis. The statistical significance in comparison to the control (vehicle) is documented by asterisks: *=$p<0.05$; **=$p<0.01$.
Figure 6:
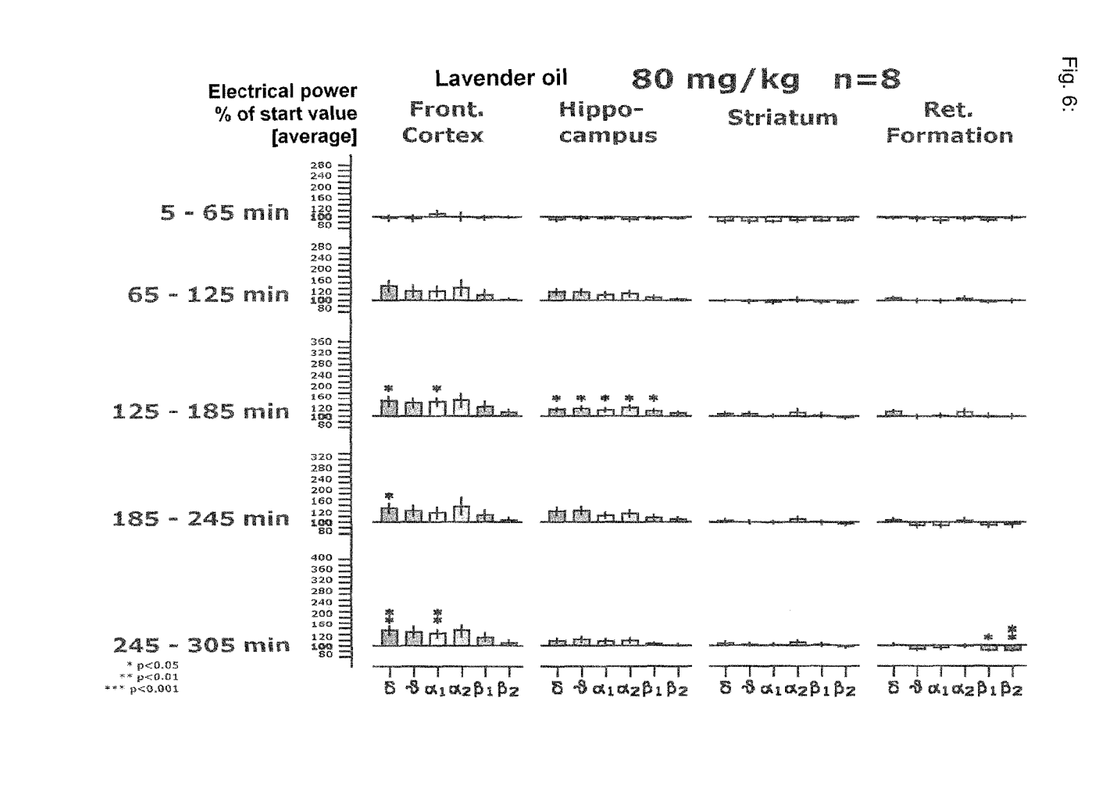
FIG. 6 Time course of electrical power of all frequency ranges during 5 hours after administration of 80 mg/kg of lavender oil alone in four areas of the brain: frontal cortex, hippocampus, striatum and formation reticularis. The six frequency ranges of delta (δ), theta (θ), alpha1 (α1), alpha2 (α2), beta1 (β1) and beta2 (β2) are documented on the x-axis. The statistical significance in comparison to the control (vehicle) is documented by asterisks: *=$p<0.05$; **=$p<0.01$.
Figure 7:
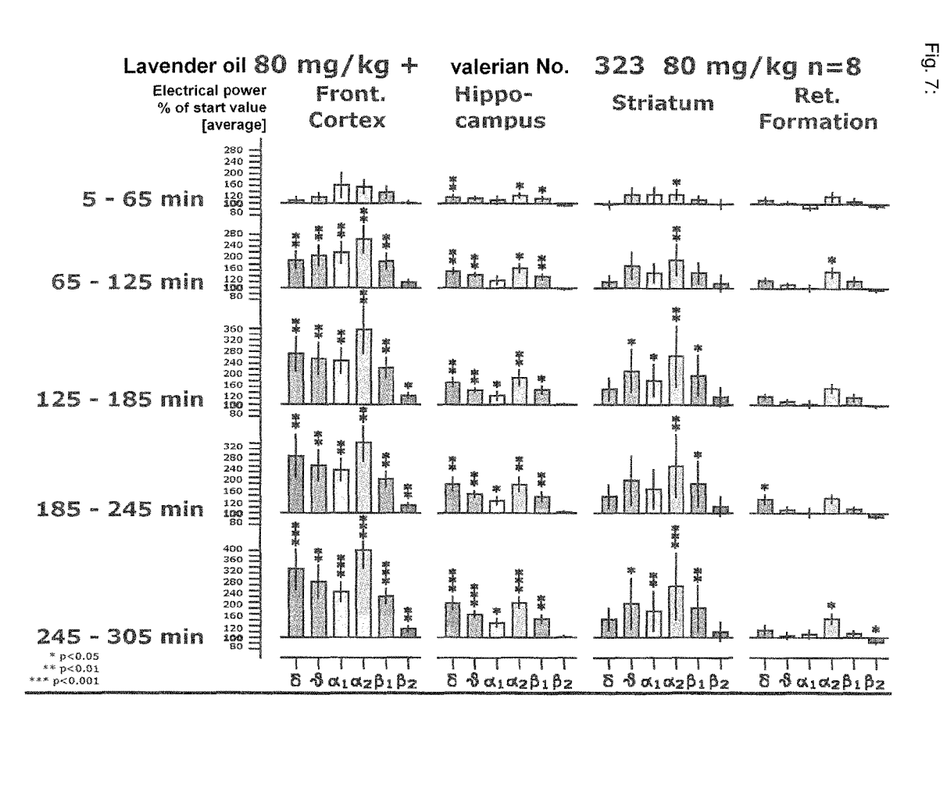
FIG. 7 Time course of electrical power of all frequency ranges during 5 hours after administration of the combination of 80 mg/kg of valerian root extract and 80 mg/kg lavender oil alone in four areas of the brain: frontal cortex, hippocampus, striatum and formation reticularis. The six frequency ranges of delta (δ), theta (θ), alpha1 (α1), alpha2 (α2), beta1 (β1) and beta2 (β2) are shown on the x-axis. The statistical significance in comparison to the control (vehicle) is documented by asterisks: *=$p<0.05$; =$p<0.01$; *=$p<0.001$.

In examination of EEG frequency changes of the rats, it was surprisingly found in comparison to the sole administration of valerian root extract that a significantly stronger increase in spectral performance was achieved after combination with lavender oil, which is useful in the treatment of sleep disorders, since the increase in those frequencies correlates to the soundness of sleep. The sole administration of a vehicle did not cause any changes in electrical power (FIG. 4).

Figure 1:
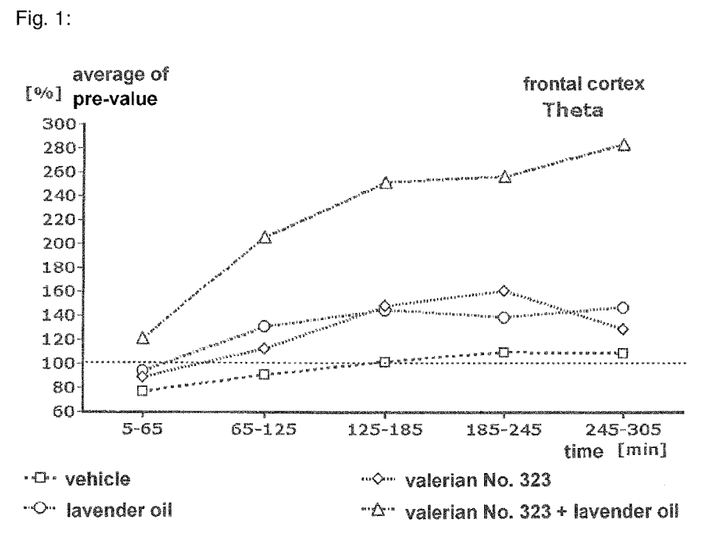
FIG. 1 Time course of theta waves over 5 hours after administration of the individual components (80 mg/kg valerian root extract; 80 mg/kg lavender oil) in comparison to the combination of valerian root extract and lavender oil (80 mg/kg+80 mg/kg) for the case of rats. The y-axis shows the power density in % of the change from the pre-value of 45 minutes before administration. It is to be noted that both components, when administered alone within the first hour, do not have any effect on this frequency, however, in case of a combination they are already efficient. The synergistic effect is overadditive.
Figure 2:
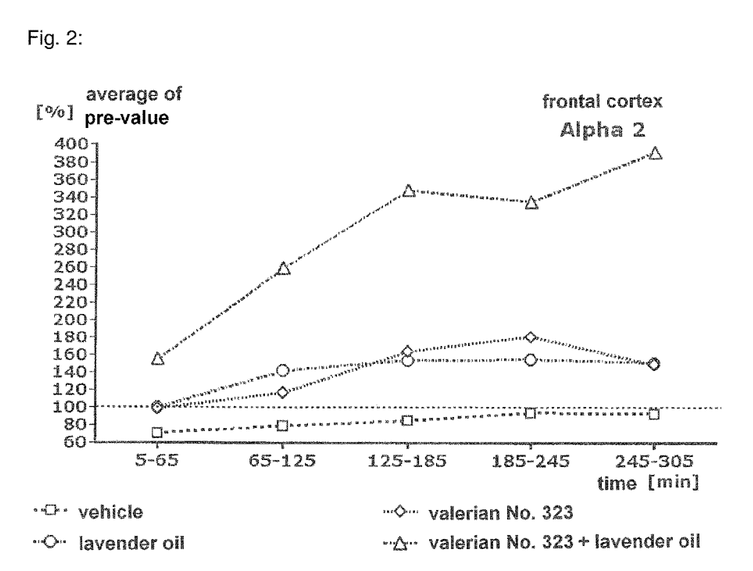
FIG. 2 Time course of alpha 2 waves during 5 hours after administration of the individual components (80 mg/kg of valerian root extract; 80 mg/kg of lavender oil) in comparison to the combination of valerian root extract and lavender oil (80 mg/kg+80 mg/kg) for the case of rats. The y-axis shows the power density in % of the change from the pre-value of 45 minutes before administration. As already described for the theta waves, an overadditive effect is developed starting from the first hour after oral administration.
Figure 3:
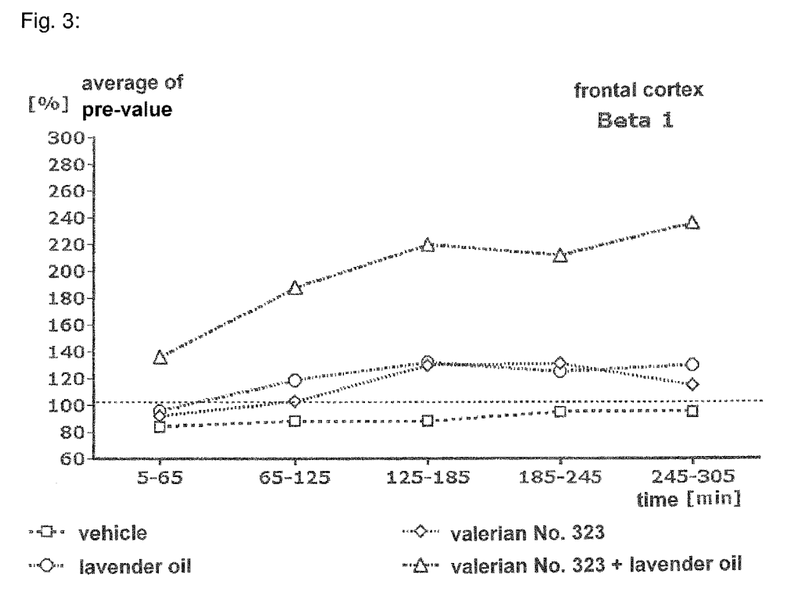
FIG. 3 Time course of beta 1 waves during 5 hours after administration of the individual components (80 mg/kg of valerian root extract; 80 mg/kg of lavender oil) in comparison to the combination of valerian root extract and lavender oil (80 mg/kg+80 mg/kg) in the rat model. The y-axis shows the power density in % of the change from the pre-value of 45 minutes before administration. As already described for the theta and alpha2 waves, an overadditive effect is developed starting from the first hour after oral administration.

FIG. 1 shows the time-dependent changes in theta EEG frequencies after oral administration of various dosages of lavender oil, or of valerian root extract alone, and as a combination. In earlier experiments, it could be shown that particularly the theta and beta1 waves of the EEG represent the soundness of sleep (Dimpfel W, Hofmann H-C Mehrdimensionale Dokumentation des Schlafes auf der Grundlage der Frequenzanalyse. In: Mayer G (ed.). Jahrbuch Schlafmedizin Deutschland 1994: MMV Verlag, Munich). Although lavender oil, when administered alone, merely results in an increase of the theta frequencies, it can be seen that the small effect of valerian root extract is outperformed despite the high dosage, and, thus, a greater soundness of sleep is achieved. The alpha2 frequencies also change in an analogous manner (FIG. 2). The same applies to the beta1 frequency which is important for the soundness of sleep. As shown in FIG. 3, the effect of the combination outperforms the effect of both individual preparations significantly, where both valerian root extract and lavender oil alone merely show any effect. This synergistic effect could be confirmed for the case of individual patients having sleep disorders. These results demonstrate that the combination of valerian root extract and lavender oil leads to a highly potent natural medicine for treatment of sleep disorders with low side effects.

According to a preferred embodiment, the sleep disorders are selected from disorders of initiating and maintaining sleep (G47.0 according to ICD-10), circadian rhythm sleep disorders (G47.2 according to ICD-10), sleep apnoea (G47.3 according to ICD-10), nonorganic insomnia (F 51.0 according to ICD-10), nonorganic disorders of the circadian rhythm (F51.2 according to ICD-10), sleepwalking (somnambulism, F51.3 according to ICD-10), pavor nocturnus (F51.4 according to ICD-10), as well as nightmares (anxiety dreams, F51.5 according to ICD-10).

According to the invention, lavender oil is used in combination with valerian root extract. The two components, lavender oil and valerian root extract, can be applied as a mixture in a dosage form (combination preparation) or as separate dosage forms. In both cases, additional pharmaceutically acceptable auxiliary agents and/or agents acceptable under food law, respectively, may be contained. According to a further preferred embodiment, no further plant extracts and/or oils from plants and/or other pharmaceutically active agents (drugs) are contained in the combination.

The valerian root extract which is contained in the combination used according to the invention is preferably prepared from dried roots of *Valeriana officinalis*. The preparation of the extract is performed using aqueous ethanol or aqueous methanol as extraction solvent, where ethanol and water in a volume ratio of 30/70 to 90/10, or methanol and water in a volume ratio of 40/60 to 55/45 are employed.

According to a preferred embodiment, as the valerian root extract, a valerian root dry extract is used. (According to the European pharmacopeia, a dry extract has a loss on drying, or a water content, respectively, of less than 5%). The dry valerian root extract preferably comprises at least 0.25 wt.-% of sesquiterpene acids (total of valerenic acid, hydroxyvalerenic acid and acetoxyvalerenic acid, calculated as valerenic acid) and thus complies with the requirements of the European Pharmacopeia, Edition 8.0. According to a further preferred embodiment, the weight ratio of valerenic acid or acetoxyvalerenic acid is at least 2/1.

The lavender oil used in the above combination according to the invention is preferably prepared by steam distillation of flowers of *Lavandula officinalis* and is optionally purified by a further distillation, in accordance with the European Pharmacopeia Monograph, Edition 8.0, "Lavender Oil". According to a preferred embodiment, the lavender oil comprises 20.0 wt.-% to 45.0 wt.-% of linalool and 25.0 wt.-% to 47.0 wt.-% of linalyl acetate as well as at most 1.0 wt.-% of limonene, at most 2.5 wt.-% of 1,8-cineol, 0.1 wt.-% to 5.0 wt.-% of 3-octanone, at most 1.2 wt.-% of camphor, 0.1 wt.-% to 8.0 wt.-% of terpinen-4-ol, at least 0.2 wt.-% of lavandulyl acetate, at least 0.1 wt.-% of lavandulol and at most 2.0 wt.-% of alpha-terpineol and thus complies with the requirements of the European Pharmacopeia, Edition 8.0.

According to the invention, lavender oil and valerian root extract can also be used in the form of highly purified preparations. The production of such preparations is known per se.

The medicament or food, respectively, i.e. the combination preparations, and the separate dosage forms, which solely comprise lavender oil or valerian root extracts as the active components, respectively, are administered orally.

For administration, the drug or food which contains the combination of valerian root extract and lavender oil, or separately the valerian root extract and the lavender oil, respectively, can be formulated e.g. as a solid preparation (e.g. a tablet, capsule, dragée, pellet, granule) or liquid preparation (solution, emulsion, suspension) where the active agent may be optionally combined with pharmaceutically acceptable auxiliaries or carriers.

In case the medicament or food, respectively, is present in a form which can be administered orally, then it preferably comprises a combination of valerian root extract and lavender oil in a weight ratio of 12.5:1 to 1:2.5, preferably 7:1 to 1:1. Other mixing ratios are possible.

The medicament or food comprising lavender oil and valerian root extract as active components is prepared according to common methods and is administered in a pharmaceutically suitable form.

Beside the active drugs (active components) the solid preparations may contain additives which are common in pharmacy and food technology. For example, common excipients are sugars (lactose, sucrose), sugar alcohols (mannitol, sorbitol, maltitol, xylitol, isomaltol), starch or cellulose. Furthermore, other technologically required additives may be present, such as thickeners (gelatine, gum arabic, cellulose, methyl cellulose, hydroxypropyl cellulose, polyvinylpyrrolidone), flow agents (highly dispersed silica, precipitated silica), disintegrating agents (croscarmellose, crospovidone), lubricating agents (magnesium stearate, calcium stearate, stearic acid, glyceryl behenate).

For improvement of intake and to cover any unpleasant flavour or smell, the solid forms (e.g. tablets) can be coated with common coating agents. For coating, solutions of sugars or sugar alcohols can be used, i.e. dragées may be prepared. Alternatively, the solid forms can be provided with a polymer coating film, i.e. coated tablets can be prepared. These films usually consist of a coating polymer (e.g. hydroxypropyl methyl cellulose), softening agent (e.g. polyethylene glycol, glycerol, triethyl citrate, glyceroltriacetate), anti-sticking agent (e.g. talcum, glycerol monostearate), anti-foaming agent (polydimethylsiloxane) and organic or inorganic colouring pigments (e.g. iron oxide, titanium dioxide, carmine).

In order to prevent an excessively fast disintegration of the solid dosage form after intake in connection with a sense of unpleasant flavour or odour and following eructation, the solid dosage form can be provided with a coating which prevents disintegration in the stomach and effects release of the active agents in the intestine. For this purpose, coating polymers which are insoluble in the gastric juice, however soluble in the chyle, such as poly(methacrylic acid-co-ethylacrylate) or shellac are commonly used.

A further preferred embodiment of the invention is the use of capsules as dosage form. Capsules provide the advantage that quite different compounds in solid or liquid form can be included in various amounts. For the case of the aforementioned capsules, there are two different embodiments, i.e. hard capsules consisting of two parts which are plugged together after filling, and soft capsules which are formed, filled and sealed in one step. In the latter case, the joint of the capsule is provided with a banderole after sealing in order to prevent leakage of the product. Soft capsules are usually made of gelatine or a mixture of carrageenan and modified starch and are filled with liquid products in the form of solutions, emulsions or suspensions.

The liquid dispersions for oral administration can e.g. be syrups, emulsions or suspensions.

Besides water, the syrup may contain sugars (e.g. sucrose), sugar alcohols (e.g. sorbitol, mannitol, xylitol) as solvents, solvent aids (glycerol, propylene glycol), as well as other additives (preservatives, acidifying agents, flavouring agents).

The dosage regimen of the medicament or food, respectively, is preferably in the range of 80 to 600 mg, particularly preferably 250 to 500 mg of valerian root extract, in combination with 40 to 200 mg, particularly preferably 40 to 80 mg of lavender oil per single dose. The single dose may be administered e.g. one to three times, preferably one to two times daily. A preferable combination comprises 250 to 500 mg of dry valerian root extract and 40 to 80 mg of lavender oil per single dose. A particularly preferable combination comprises 500 mg of dry valerian root extract and 80 mg of lavender oil, or 250 mg of dry valerian root extract and 40 mg of lavender oil, respectively.

In case of using further extracts, the amounts used have to be adapted correspondingly in the manner known to the skilled person.

The combination according to the invention can be used both as medicament and as food. In this respect, the term food particularly includes dietetic food, food supplements as well as medical food and dietary supplements.

Test Methods

1. Pentobarbital-Induced Sleep Time of Mouse

In order to examine the influence of lavender oil (prepared according to Example 2), valerian root extract (prepared according to Example 1), and the combination of both substances, respectively, on the sleep of mice, the model of pentobarbital-induced sleep time by was chosen. In this respect, the animals are treated with the testing substances and, subsequently, pentobarbital is applied in order to measure whether the induced sleep time changes. Sedating test agents extend the sleep time induced by pentobarbital.

Changes in sleep time after administration of agarose gel (control) and of lavender oil, valerian root extract, or lavender oil and valerian root extract in combination, respectively, was determined.

32 male NMRI mice from the breeder Janvier, LaGenest, France were used for the test after acclimatisation time of at least one week. The experiment itself was started with orally treating the mice with the control or test substances (lavender oil or valerian root extract, or the combination of both). One hour later, all test animals received an interperitoneal application of 45 mg/kg pentobarbital to induce sleep. Subsequently, the mice were observed in regular intervals and upon recognising sedation of the animals, the positional reflex was tested (the animals were placed supine, and in case they remain lying this was defined as sleep/sedation) and the time of falling asleep was recorded. If the sedation decreases and the animals wake up, they turn into abdominal position, and this time point which was defined as time of wake-up was also documented. The time period from falling asleep until wake-up is the sleep time. Two hours after individual start of sleep, the experiment was terminated. Animals which were asleep for a longer time, were defined as having a sleep time of 2 hours.

The sole administration of valerian root extract or lavender oil does not lead to changes in sleep time induced by pentobarbital. However, administration of valerian root extract and lavender oil leads to a highly significant extension of sleep time (see Table 1).

TABLE 1

Sleep time induced by pentobarbital after administration of agarose gel (control) and of lavender oil, valerian root extract or lavender oil and valerian root extract in combination, respectively

| Substance | Dosage mg/kg | Sleep time (minutes) |
| --- | --- | --- |
| Control | | 46.9 ± 21 |
| Valerian root extract | 80 | 38.4 ± 27 |

TABLE 1-continued

Sleep time induced by pentobarbital after administration of agarose gel (control) and of lavender oil, valerian root extract or lavender oil and valerian root extract in combination, respectively

| Substance | Dosage mg/kg | Sleep time (minutes) |
|---|---|---|
| Lavender oil | 80 | 57.4 ± 23 |
| Valerian root extract + lavender oil | 80 + 80 | 90.8 ± 32 [#] |

[#] p < 0.01 T-Test

2. Tele-Stereo-EEG of Rats

The changes in EEG frequencies after administration of methyl cellulose (control), or of lavender oil (prepared according to Example 2), valerian root extract (prepared according to Example 2) or lavender oil and valerian root extract in combination, respectively, were determined.

Examinations were performed in analogy to the method described by W. Dimpfel (Dimpfel W: Preclinical data base of pharmaco-specific rat EEG fingerprints (Tele-Stereo-EEG). Eur J Med Res (2003) 8: 199-207) as follows:

Concentric electrodes together with a microplug on a common basis plate were implanted into eight male adult Fischer-344 rats (day-night converted) at the age of 6 months. The plug served to receive a 4-channel transmitter for telemetric transmission of the field potentials derived from frontal cortex, hippocampus, striatum and formation reticularis. The signals were subjected to fast Fourier transformation on a computer system (software: "EEG-Analyse", operating system: OS Science, laboratory computer "LabTeam" of MediSyst, Linden, Germany) in real time and the performance density spectra were averaged over 60 minutes each. The subdivision of the spectra in 6 different frequency ranges allowed the recording of pharmaco-specific changes with respect to the preceding values within those frequency bands measured before administration.

45 minutes after start of the measurements, the preparations were administered orally (stored value). The measurement was resumed 5 minutes later and analysed continuously at least over the next 5 hours and subsumed in periods of 60 minutes. The test substances were administered in different combinations. The experimental series was started with administration of methyl cellulose (control), which did not lead to any noticeable change.

The statistical comparison of the experiments relating to the results measured after administration of methyl cellulose was made according to Wilcoxon, Mann and Whitney on the basis of the changes within the individual frequency bands in all brain regions as the variables.

Administration of methyl cellulose hardly effected any changes in electrical power ($\mu V2$) in comparison to the phase pre-values (FIG. 4). The sole administration of valerian root extract or lavender oil effected very weak, barely measurable changes of the spectral performance, which were only recognisable starting from the second hour after administration (see FIGS. 1, 2, 3 as well as 5 and 6).

In contrast, administration of lavender oil in combination with valerian root extract led to very early and stable changes in performance density already in the first hour after administration, in particular in the cortex, but also during the third to fifth hour after application (see FIGS. 1, 2, 3 and FIG. 7).

The oral administration of the combination of valerian root extract and lavender oil as a single dose led to extremely clear and statistically significant changes in electrical brain activity of the test animals corresponding to those during sleep. This is particularly surprising, since the preparations were administered on the morning, i.e. after night sleep (inactive phase).

EXAMPLE 1: PREPARATION OF VALERIAN ROOT EXTRACT ACCORDING TO PH. EUR

Dried roots of *Valeriana officinalis* were extracted twice with the sevenfold amount by weight of 70% (v/v) ethanol at 60° C. for 1 h. The cooled mixture was filtrated. The filtrate was concentrated and dried at 60° C. and 25 mbar for 8 h: 24% yield of dry extract.

EXAMPLE 2: PREPARATION OF LAVENDER OIL ACCORDING TO PH. EUR

Fresh flowers of *Lavandula officinalis* were subjected to steam distillation according to Ph. Eur. The essential oil thus obtained was further purified by distillation at max. 120° C. and 10 to 20 mbar.

EXAMPLE 3: COMBINATION PREPARATION IN FORM OF A COATED TABLET

TABLE 2

Composition of coated tablets including 500 mg valerian root extract and 80 mg lavender oil

| Item | Ingredient | Amount per tablet [mg] | Amount per production scale for 30,000 tablets [kg] |
|---|---|---|---|
| 1 | valerian root extract | 500.0 | 15.00 |
| 2 | precipitated silica | 100.0 | 3.00 |
| 3 | lavender oil | 80.0 | 2.40 |
| 4 | microcrystalline cellulose | 200.0 | 6.00 |
| 5 | croscarmellose sodium | 40.0 | 1.20 |
| 6 | precipitated silica | 20.0 | 0.60 |
| 7 | magnesium stearate | 5.0 | 0.15 |
| 8 | hypromellose | 40.0 | 1.20 |
| 9 | Macrogol 1500 | 8.0 | 0.24 |
| 10 | titanium dioxide E171 | 6.0 | 0.18 |
| 11 | iron oxide yellow E172 | 3.0 | 0.09 |
| 12 | talcum | 3.0 | 0.09 |
|  |  | 1005.0 | 30.15 |

For production of a tablet including 500 mg of solid dry valerian root extract and 80 mg of liquid lavender oil, 15 kg of dry valerian root extract (item 1) were intensively mixed with 3 kg of precipitated silica (item 2). Subsequently, 2.4 kg of lavender oil (item 3) were added to this mixture, again followed by thorough mixing. A powdery mixture without liquid contents is obtained. In case the mixture of dry valerian root extract and lavender oil is prepared without precipitated silica, the lavender oil separates in liquid form and the mixture is not suitable for further processing into tablets.

To the mixture of dry valerian root extract, silica and lavender oil, microcrystalline cellulose (excipient and binding agent; item 4), croscarmellose sodium (disintegrating accelerator, item 5), precipitated silica (flowing agent; item 6) are added and mixing is performed. Finally, magnesium stearate (lubricating agent; item 7) is added and mixing is performed for another short period of 5 minutes.

Using a rotary tablet press, the resulting mixture is pressed into oval tablets having an individual mass of 945 mg. For preparation of a coating, the ingredients of the coating, i.e. hypromellose (film-forming agent, item 8), Macrogol 1500 (softening agent, item 9), titanium dioxide and iron oxide (colouring pigments, items 10 and 11) as well as talcum (anti-sticking agent, item 12), are dispersed in water and coated on the tablets using a drum coater. As the product, uniformly coated yellow coloured film tablets including 500 mg dry valerian root extract and 80 mg lavender oil for oral administration are obtained.

EXAMPLE 4: COMBINATION PREPARATION IN FORM OF A SOFT CAPSULE

TABLE 3

Composition of mixture for filling of soft or hard capsules with 250 mg of dry valerian root extract and 40 mg of lavender oil

| Item | Ingredient | Amount per capsule [mg] | Amount per production scale for 100,000 capsules [kg] |
|---|---|---|---|
| 1 | hydrogenated fat | 230.0 | 23.0 |
| 2 | hydrogenated soybean oil | 60.0 | 6.0 |
| 3 | refined rapeseed oil | 40.0 | 4.0 |
| 4 | dry valerian root extract | 250.0 | 25.0 |
| 5 | lavender oil | 40.0 | 4.0 |
|   |   | 620.0 | 62.0 |

For producing the composition for filling the capsules, hydrogenated fat (item 1), hydrogenated soybean oil (item 2) and refined rapeseed oil (item 3) are melted at 50° C. or dissolved, respectively. The dry valerian root extract is homogeneously dispersed in the molten mass and, subsequently, the lavender oil is added and homogeneously dispersed. The resulting composition for filling the capsules is stored in a tightly sealable temperable container under stirring and is filled into solid capsules at approx. 30-40° C., or is used for filling of soft capsules. The desired amount of 500 mg of dry valerian root extract and 80 mg of lavender oil can be applied orally by intake of two capsules.

The invention claimed is:

1. A method for the treatment or prophylaxis of sleep disorders in a subject comprising administration to the subject of a combination comprising 250 to 500 mg of valerian root extract (extract of dried roots of *Valeriana officinalis*) and 40 to 80 mg of lavender oil (oil of flowers of *Lavandula officinalis*) per single dose.

2. The method of claim 1, wherein the valerian root extract is prepared by extraction with aqueous ethanol or aqueous methanol, wherein ethanol and water are used in a volume ratio of 30/70 to 90/10 or methanol and water are used in a volume ratio of 40/60 to 55/45 in the extraction.

3. The method of claim 2, wherein the sleep disorders are selected from disorders of initiating and maintaining sleep, circadian rhythm sleep disorders, sleep apnoea, nonorganic insomnia, nonorganic disorder of the circadian rhythm, sleepwalking (somnambulism), pavor nocturnus, or nightmares (anxiety dreams).

4. The method of claim 2, wherein a dry valerian root extract is employed as the valerian root extract.

5. The method of claim 4, wherein the dry valerian root extract contains at least 0.25 wt.-% of sesquiterpene acids.

6. The method of claim 5, wherein the weight ratio of valerenic acid to acetoxy valerenic acid in the dry valerian root extract is at least 2/1.

7. The method of claim 2, wherein the lavender oil comprises 20.0 wt.-% to 45.0 wt.-% of linalool and 25.0 wt.-% to 47.0 wt.-% of linalyl acetate.

8. The method of claim 2, wherein the lavender oil additionally comprises at most 1.0 wt.-% limonene, at most 2.5 wt.-% 1,8-cineol, 0.1 wt.-% to 5.0 wt.-% 3-octanone, at most 1.2 wt.-% camphor, 0.1 wt.-% to 8.0 wt.-% terpinen-4-ol, at least 0.2 wt.-% lavandulyl acetate, at least 0.1 wt.-% lavandulol and at most 2.0 wt.-% alpha-terpineol.

* * * * *